(12) United States Patent
Kim et al.

(10) Patent No.: US 9,539,236 B2
(45) Date of Patent: Jan. 10, 2017

(54) PHARMACEUTICAL COMPOSITION FOR PREVENTING OR TREATING CANCER

(71) Applicant: Medicinal Bioconvergence Research Center, Suwon-si (KR)

(72) Inventors: Sunghoon Kim, Seoul (KR); Nam Hoon Kwon, Seoul (KR); Dae Gyu Kim, Seoul (KR)

(73) Assignee: Medicinal Bioconvergence Research Center, Suwon-si (KR)

( * ) Notice: Subject to any disclaimer, the term of this patent is extended or adjusted under 35 U.S.C. 154(b) by 0 days.

(21) Appl. No.: 14/727,146

(22) Filed: Jun. 1, 2015

(65) Prior Publication Data

US 2015/0258060 A1  Sep. 17, 2015

Related U.S. Application Data

(63) Continuation of application No. PCT/KR2014/005105, filed on Jun. 11, 2014.

(30) Foreign Application Priority Data

Jun. 14, 2013 (KR) ........................ 10-2013-0068659

(51) Int. Cl.
*C07D 273/01* (2006.01)
*A61K 31/395* (2006.01)

(52) U.S. Cl.
CPC ........... *A61K 31/395* (2013.01); *C07D 273/01* (2013.01)

(58) Field of Classification Search
CPC .................................................... C07D 273/01
See application file for complete search history.

(56) References Cited

U.S. PATENT DOCUMENTS

| | | |
|---|---|---|
| 5,248,673 A | 9/1993 | Balasubramanian et al. |
| 7,459,529 B2 | 12/2008 | Kim |
| 2004/0116706 A1 | 6/2004 | Mammen et al. |
| 2011/0200582 A1 | 8/2011 | Baryza et al. |
| 2014/0142333 A1 | 5/2014 | Kim et al. |

FOREIGN PATENT DOCUMENTS

| | | |
|---|---|---|
| KR | 1020060058014 | 5/2006 |
| KR | 1020090048382 | 5/2009 |
| KR | 1020130016041 | 2/2013 |
| KR | 1020130016134 | 2/2013 |
| WO | 82-04253 | 12/1982 |

OTHER PUBLICATIONS

Choi et al., "Cancer-Associated Splicing Variant of Tumor Suppressor AIMP2/p38: Pathological Implication in Tumorigenesis", PLOS Genetics, Mar. 31, 2011, vol. 7, Issue 3.
Nicolaides et al., "Analysis of the 5* Region of PMS2 Reveals Heterogeneous Transcripts and a Novel Overlapping Gene", Genomics, Jun. 20, 1995, vol. 29, p. 329-334.
Mammalian Gene Collection Program Team, "Generation and initial analysis of more than 15,000 full-length human and mouse cDNA sequences", Proceedings of the National Academy of Sciences, Dec. 24, 2002, vol. 99, Issue 26, p. 16899-16903.
International Search Report issued Sep. 22, 2014 in International Application No. PCT/KR2014/005105.

*Primary Examiner* — Samira Jean-Louis
(74) *Attorney, Agent, or Firm* — H.C. Park & Associates, PLC

(57) ABSTRACT

Exemplary embodiments relate to a novel anticancer composition including a compound represented by chemical formula 1 or pharmaceutically acceptable salt thereof as an active ingredient:

<Chemical formula 1>

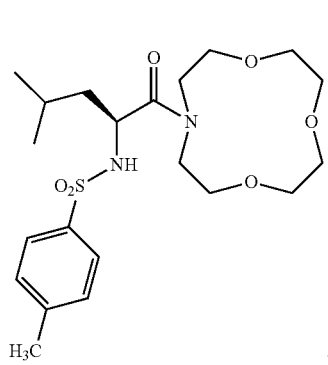

16 Claims, 4 Drawing Sheets

SEQUENCE LISTING

```
<160> NUMBER OF SEQ ID NOS: 5

<210> SEQ ID NO 1
<211> LENGTH: 756
<212> TYPE: DNA
<213> ORGANISM: Homo sapiens
```

<400> SEQUENCE: 1

```
atgccgatgt accaggtaaa gccctatcac gggggcggcg cgcctctccg tgtggagctt    60
cccacctgca tgtaccggct ccccaacgtg cacggcagga gctacggccc agcgccgggc   120
gctggccacg tgcaggatta cggggcgctg aaagacatcg tgatcaacgc aaacccggcc   180
tcccctcccc tctccctgct tgtgctgcac aggctgctct gtgagcactt cagggtcctg   240
tccacggtgc acacgcactc ctcggtcaag agcgtgcctg aaaaccttct caagtgcttt   300
ggagaacaga ataaaaaaca gccccgccaa gactatcagc tgggattcac tttaatttgg   360
aagaatgtgc cgaagacgca gatgaaattc agcatccaga cgatgtgccc catcgaaggc   420
gaagggaaca ttgcacgttt cttgttctct ctgtttggcc agaagcataa tgctgtcaac   480
gcaacccttt agatagctgg gtagatatt gcgattttc agttaaaaga gggaagcagt   540
aaagaaaaag ccgctgtttt ccgctccatg aactctgctc ttgggaagag cccttggctc   600
gctgggaatg aactcaccgt agcagacgtg gtgctgtggt ctgtactcca gcagatcgga   660
ggctgcagtg tgacagtgcc agccaatgtg cagaggtgga tgaggtcttg tgaaaacctg   720
gctccttta acacggccct caagctcctt aagtga                              756
```

<210> SEQ ID NO 2
<211> LENGTH: 21
<212> TYPE: DNA
<213> ORGANISM: Artificial Sequence
<220> FEATURE:
<223> OTHER INFORMATION: Forward primer for AIMP2

<400> SEQUENCE: 2

```
atgccgatgt accaggtaaa g                                              21
```

<210> SEQ ID NO 3
<211> LENGTH: 21
<212> TYPE: DNA
<213> ORGANISM: Artificial Sequence
<220> FEATURE:
<223> OTHER INFORMATION: Reverse primer for AIMP2

<400> SEQUENCE: 3

```
cttaaggagc ttgagggccg t                                              21
```

<210> SEQ ID NO 4
<211> LENGTH: 24
<212> TYPE: DNA
<213> ORGANISM: Artificial Sequence
<220> FEATURE:
<223> OTHER INFORMATION: Forward primer for AIMP2-DX2

<400> SEQUENCE: 4

```
ctggccacgt gcaggattac gggg                                           24
```

<210> SEQ ID NO 5
<211> LENGTH: 20
<212> TYPE: DNA
<213> ORGANISM: Artificial Sequence
<220> FEATURE:
<223> OTHER INFORMATION: Reverse primer for AIMP2-DX2

<400> SEQUENCE: 5

```
aagtgaatcc cagctgatag                                                20
```

PHARMACEUTICAL COMPOSITION FOR PREVENTING OR TREATING CANCER

CROSS REFERENCE TO RELATED APPLICATIONS

This application is a Continuation of International Application No. PCT/KR2014/005105, filed on Jun. 11, 2014, and claims priority from and the benefit of Korean Patent Application No. 10-2013-0068659, filed on Jun. 14, 2013, which are hereby incorporated by reference for all purposes as if fully set forth herein.

BACKGROUND

Field

Exemplary embodiments relate to a novel use of a compound for preventing or treating cancer, and more specifically, to a pharmaceutical composition for preventing or treating cancer, including a compound represented by chemical formula 1 or a pharmaceutically acceptable salt thereof as an active ingredient.

Discussion of the Background

Aminoacyl-tRNA synthetase (ARS) plays an important role in binding a specific amino acid to a tRNA molecule, leading to protein synthesis. In higher animals, nine classes of ARSs bind with three classes of ARS-interacting multi functional proteins (AIMPs) to form multi-synthetases complexes (MSCs). AIMP2, which is a multifunctional protein that maintains the MSC structure and performs various functions in response to stress signals, leads to apoptosis under TGF-β, TNF-α, and DNA damage signals and acts as a tumor suppressor by maintaining p53 stability under DNA damage signals including UV and the like, and AIMP2-DX2, which is an exon 2-deleted splicing variant of AIMP2, competitively inhibits the binding of p53 and AIMP2 to inhibit the pro-apoptotic activity of AIMP2 (Choi J W, et al., PLOS GENETICS, 7(3):e1001351, 2011). The studies found that AIMP2-DX2 may cause cancer by inhibiting cancer inhibition of AIMP2, and AIMP2-DX2 mRNA exhibits a high expression level of 80% in tissues of lung cancer patients and AIMP2-DX2 is also expressed at 60% in lung cancer. In addition, the expression level of AIMP2-DX2 over AIMP2 showed a close correlation with the progress of lung cancer.

The AIMP2-DX2 protein is a variant of AIMP2 in which exon 2 is deleted from the AIMP2 protein sequence, and sequences of the AIMP2 protein (312aa version: AAC50391.1 or GI: 1215669; 320aa version: AAH13630.1, GI: 15489023, BC013630.1) are disclosed in the literatures (312aa version: Nicolaides, N. C., et. al., Genomics 29 (2), 329-334 (1995)/320aa version: Generation and initial analysis of more than 15,000 full-length human and mouse cDNA sequences, Proc. Natl. Acad. Sci. U.S.A. 99 (26), 16899-16903 (2002)).

The term anticancer encompasses all cancer prevention and treatment effects. Cancer generally refers to the malignancy of cells that are not normally differentiated and have grown out of control since there is abnormality in the cycle stage of cells constituting human tissues. The kind of the cancer may include breast cancer, large intestine cancer, lung cancer, small cell lung cancer, gastric cancer, liver cancer, blood cancer, bone cancer, pancreatic cancer, skin cancer, head or neck cancer, cutaneous or intraocular melanoma, uterine cancer, ovarian cancer, rectal cancer, anal cancer, colon cancer, fallopian tube carcinoma, endometrial carcinoma, cervical cancer, vaginal cancer, vulvar carcinoma, Hodgkin's disease, esophageal cancer, small intestine cancer, endocrine cancer, thyroid cancer, parathyroid carcinoma, adrenal cancer, soft tissue sarcoma, uterine cancer, penis cancer, prostate cancer, chronic or acute leukemia, lymphocyte lymphoma, bladder cancer, kidney or ureter cancer, renal cell carcinoma, renal pelvic carcinoma, CNS tumor, primary CNS lymphoma, spinal cord tumor, brain stem glioma, pituitary adenoma, and the like.

A Korean patent (Korean Patent Publication No. 10-2006-0058014) describes an exon 2-deleted variant of AIMP2, named AIMP2DX2, which is specifically expressed in cancer tissues, and is used as a cancer diagnosis marker to diagnose cancer and inhibits AIMP2DX2 to treat or prevent cancer. In addition, there are a patent (Korean Patent Publication No. 10-2009-0048382) regarding a composition including an AIMP2-DX2 inhibitor as an active ingredient for preventing and treating inflammatory disease, a composition including an expression vector inhibiting AIMP2-DX2 expression for preventing and treating inflammatory disease, and a method for screening a drug for preventing or treating inflammatory disease to screen a material inhibiting AIMP2-DX2 expression; and a patent (Korean Patent Publication No. 2013-0016041) regarding an anticancer composition including, as an active ingredient, an aniline derivative effective in the cancer prevention and treatment.

The above information disclosed in this Background section is only for enhancement of understanding of the background of the inventive concept, and, therefore, it may contain information that does not form the prior art that is already known in this country to a person of ordinary skill in the art.

SUMMARY

One or more exemplary embodiments relate to a pharmaceutical composition for preventing or treating cancer.

Additional aspects will be set forth in the detailed description which follows, and, in part, will be apparent from the disclosure, or may be learned by practice of the inventive concept.

An exemplary embodiment discloses a pharmaceutical composition for preventing or treating cancer, including a compound represented by chemical formula 1 below or a pharmaceutically acceptable salt thereof as an active ingredient.

[Chemical formula 1]

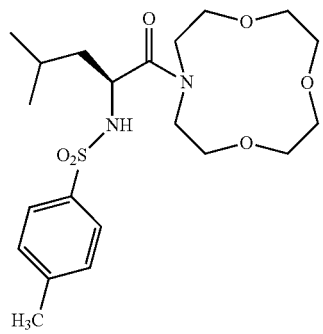

An exemplary embodiment discloses a method for preventing or treating cancer, the method including administering the compound represented by the chemical formula 1 or the pharmaceutically acceptable salt thereof to a subject in need thereof.

An exemplary embodiment discloses a use of the compound represented by the chemical formula 1 or the pharmaceutically acceptable salt thereof for preparing an agent for cancer prevention or treatment.

The foregoing general description and the following detailed description are exemplary and explanatory and are intended to provide further explanation of the claimed subject matter.

BRIEF DESCRIPTION OF THE DRAWINGS

The accompanying drawings, which are included to provide a further understanding of the inventive concept, and are incorporated in and constitute a part of this specification, illustrate exemplary embodiments of the inventive concept, and, together with the description, serve to explain principles of the inventive concept.

DETAILED DESCRIPTION OF ILLUSTRATED EMBODIMENTS

Figure 1:
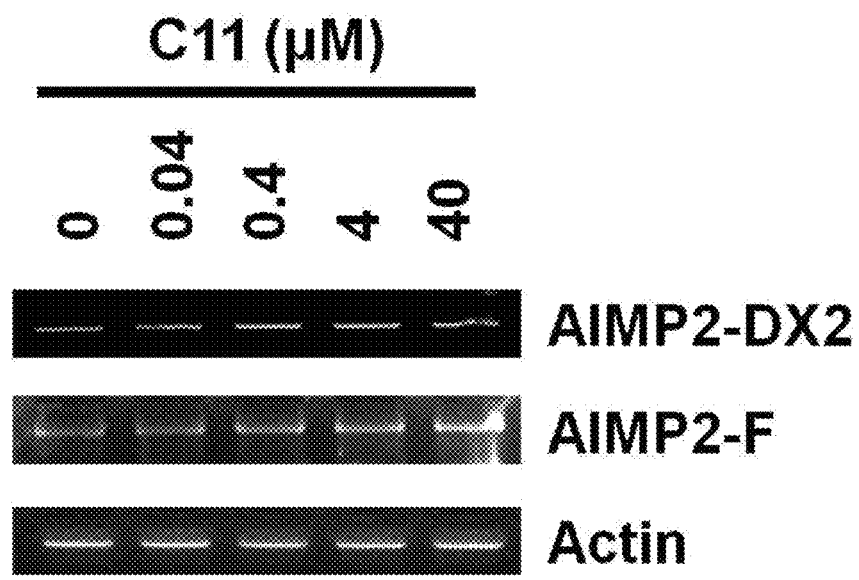
FIG. 1 shows RT-PCR results verifying whether the compound of an exemplary embodiment of the present invention inhibits the mRNA level of AIMP2-DX2 in a concentration-dependent manner. Actin was used as a positive control (AIMP2-DX2: mRNA level of AIMP2-DX2; AIMP2-F: mRNA level of full-length AIMP2 without exon deletion).

Exemplary embodiments of the present invention will be described more fully hereinafter with reference to the accompanying drawings, in which exemplary embodiments of the invention are shown. This invention may, however, be embodied in many different forms and should not be construed as limited to the exemplary embodiments set forth herein. Rather, these exemplary embodiments are provided so that this disclosure is thorough, and will fully convey the scope of the invention to those skilled in the art.

An exemplary embodiment of the present invention provides a pharmaceutical composition for cancer prevention or treatment, including a compound represented by chemical formula 1 below or a pharmaceutically acceptable salt thereof as an active ingredient.

The present inventors, while searching compounds capable of suppressing the growth of cancer cells by inhibiting expression of AIMP2-DX2, have found that a compound (C11) represented by chemical formula 1 herein suppresses the intracellular level of AIMP2-DX2 and inhibits the proliferation of cancer cells, and thus is useful as an anticancer agent for cancer prevention and treatment.

Further, an exemplary embodiment of the present invention provides a method for preventing or treating cancer, the method including a step of administering a compound represented by chemical formula 1 below or a pharmaceutically acceptable salt thereof to a subject in need thereof.

Further, an exemplary embodiment of the present invention provides a use of a compound represented by chemical formula 1 or a pharmaceutically acceptable salt of the compound represented by chemical formula 1 for preparing an agent for cancer prevention or treatment.

[Chemical formula 1]

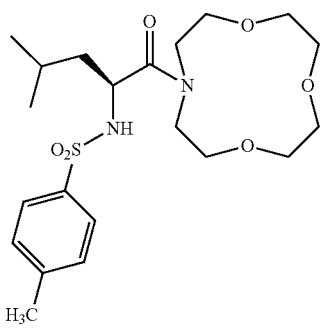

The compound is represented by the chemical formula 1 above, and called 1,4,7-Trioxa-10-azacyclododecane, 10-[4-methyl-2-[[(4-methylphenyl)sulfonyl]amino]-1-oxopentyl].

The compound of chemical formula 1 may be used as a pharmaceutically acceptable salt. As the salt, acid addition salts which are formed by various pharmaceutically or physiologically acceptable organic or inorganic salts are useful. Examples of suitable organic acids may include carboxylic acid, phosphonic acid, sulfonic acid, acetic acid, propionic acid, octanoic acid, decanoic acid, glycolic acid, lactic acid, fumaric acid, succinic acid, adipic acid, malic acid, tartaric acid, citric acid, glutamic acid, aspartic acid, maleic acid, benzoic acid, salicylic acid, phthalic acid, phenylacetic acid, benzene sulfonic acid, 2-naphthalenesulfonic acid, methyl sulfuric acid, ethyl sulfuric acid, dodecyl sulfuric acid, and the like. Examples of suitable inorganic acids may include hydrochloric acid, sulfuric acid, or phosphoric acid.

The compound of chemical formula 1 may include all salts, hydrates, and solvates, which may be prepared by normal methods, as well as the pharmaceutically acceptable thereof.

The compound of chemical formula 1 suppresses the intracellular level of AIMP2-DX2, which is known to be overexpressed in cancer cells, and selectively exhibits cytotoxicity only in cancer cells without influencing normal cells.

The foregoing effects of one or more exemplary embodiments are well shown in examples of the present disclosure.

In an example, a lung cancer cell line was treated with the compound, C11, and then the cells were cultured and collected, and the protein and mRNA levels were measured. The results verified that compound C11 had no effect on the mRNA level of AIMP2-DX2, but reduced the protein level of AIMP2-DX2 in a concentration-dependent manner and had no effect on the expression of the AIMP2 protein. Thus, it can be seen that the compound, C11, inhibits the expression of AIMP2-DX2, which is known to be overexpressed in lung cancer patients.

In another example, a lung cancer line was treated with the compound, C11, with different concentrations, and the cell viability was measured. The results verified that the viability of lung cancer cells decreased in a concentration-dependent manner of administered C11.

Therefore, the compound, C11, was verified to have excellent cancer prevention and treatment effects.

In addition, in another example, as a result of a cytotoxicity test on a normal cell line, it was verified that the compound, C11, had no cytotoxicity on normal cells.

Therefore, it was verified that the compound, C11, inhibits the expression of AIMP2-DX2 in lung cancer cells, inhibits the proliferation of lung cancer cells in a concentration-dependent manner, has no toxicity on normal cells, and is selective only to lung cancers.

Thus, the composition has excellent cancer prevention and treatment effects.

Examples of the cancer may include, but are not particularly limited to, breast cancer, large intestine cancer, lung cancer, small cell lung cancer, gastric cancer, liver cancer, blood cancer, bone cancer, pancreatic cancer, skin cancer, head or neck cancer, cutaneous or intraocular melanoma, uterine cancer, ovarian cancer, rectal cancer, anal cancer, colon cancer, fallopian tube carcinoma, endometrial carcinoma, cervical cancer, vaginal cancer, vulvar carcinoma, Hodgkin's disease, esophageal cancer, small intestine cancer, endocrine cancer, thyroid cancer, parathyroid carcinoma, adrenal cancer, soft tissue sarcoma, uterine cancer, penis cancer, prostate cancer, chronic or acute leukemia, lymphocyte lymphoma, bladder cancer, kidney or ureter cancer, renal cell carcinoma, renal pelvic carcinoma, CNS tumor, primary CNS lymphoma, spinal cord tumor, brain stem glioma, pituitary adenoma, and the like, and may be preferably lung cancer.

For the pharmaceutical composition of an exemplary embodiment, the compound of the chemical formula 1 or pharmaceutically acceptable salt thereof may be formulated into various formulations appropriate for oral or parenteral administration, when clinically administered. In case of being formulated into a general medicine form, a conventionally used diluent or excipient, such as a filler, an extender, a binder, a wetting agent, a disintegrating agent, a surfactant, etc. may be used for the preparation.

Examples of a solid preparation for oral administration may include tablets, pills, powders, granules, capsules, troche and the like, and such a solid preparation is prepared by mixing the aril derivatives of an exemplary embodiment or pharmaceutically acceptable salt thereof with at least one excipient, for example, starch, calcium carbonate, sucrose, lactose, gelatin, or the like. Also, besides a simple excipient, lubricants such as magnesium stearate, talc may be used. Examples of a liquid preparation for oral administration may include a suspension, a liquid for internal use, an emulsion, a syrup, and the like, and the liquid preparation may include not only a generally used simple diluent, such as water, and liquid paraffin, but also various excipients, for example, a wetting agent, a sweetening agent, an aromatic agent, a preservative, etc.

Examples of a preparation for parenteral administration include a sterilized aqueous solution, a non-aqueous solvent, a suspension, an emulsion, a freeze-drying agent and a suppository. As a non-aqueous solvent or a suspension solvent, propylene glycol, polyethylene glycol, vegetable oil (such as olive oil), injectable ester (such as ethyl oleate), or the like may be used. As a substrate for the suppository, Witepsol, Macrogol, twin 61, cacao butter, laurin butter, glycerol, gelatin, or the like may be used.

In addition, the dose of the compound of an exemplary embodiment or the pharmaceutically acceptable salt thereof to the human body may vary depending on the age, body weight, and the gender of the patient, the manner of administration, the health condition, and the severity of the disease. Based on the adult patient weighting 70 Kg, a dose thereof is generally 0.1 to 1000 mg/day, and preferably 1 to 500 mg/day. The compound or the pharmaceutically acceptable salt thereof may be administered once a day or divided into multiple doses at predetermined time intervals according to the determination of a doctor or pharmacist.

The pharmaceutical composition of an exemplary embodiment may be used alone or in combination with other methods employing surgery, hormone treatment, chemical treatment, and biological response controller, for cancer prevention or treatment.

As used herein, the term "subject" means animals, preferably mammals, particularly animals including humans. In addition, the subject may also be a cell, a tissue or an organ derived from an animal. The subject may be a patient in need of treatment. As used herein, the expression "subject in need thereof" may refer to a subject who is in need of treating or preventing cancer, tumor or a neoplasmic disease As used herein, the term "effective amount" may refer to the amount of compound of chemical formula 1 or pharmaceutically acceptable salt thereof that exhibits an effective effect, that is, the effect of treating or preventing cancer, tumor or a neoplasmic disease, in a subject in need thereof.

The compound of chemical formula 1 or pharmaceutically acceptable salt thereof may be administered as it is, or may be prepared into various formulations as described above for administration. Preferably, it may be administered until a desired effect, that is, a cancer prevention/treatment effect, is obtained. The compound of an exemplary embodiment or its pharmaceutically acceptable salt may be administered by various routes according to a method known in the art. In other words, it may be administered orally or parenterally, for example, buccally, intramuscularly, intravenously, intracutaneously, intraarterially, intrasseously, intrathecally, intraperitoneally, intranasally, intravaginally, rectally, sublingually or subcutaneously, or may be administered by a gastrointestinal, transmucosal or respiratory route.

Meanwhile, the composition of an exemplary embodiment could be formulated into various form on its purpose. Examples of formulates for the composition of an exemplary embodiment are as follows:

Preparation Example 1

Preparation of Pharmaceutical Agent

1. Preparation of Powders

| | |
|---|---|
| The compound of chemical formula 1 | 2 g |
| lactose | 1 g |

The above mentioned components were mixed and filled in an airtight pouch, thereby preparing a powder formulation.

2. Preparation of Tablets

| | |
|---|---|
| The compound of chemical formula 1 | 100 mg |
| Corn starch | 100 mg |
| Lactose | 100 mg |
| Magnesium stearate | 2 mg |

The above mentioned components were mixed and performed direct compression according to a conventional method or other methods, thereby preparing a tablet formulation.

3. Preparation of Capsules

| | |
|---|---|
| The compound of chemical formula 1 | 100 mg |
| Corn starch | 100 mg |
| Lactose | 100 mg |
| Magnesium stearate | 2 mg |

The above mentioned components were mixed and filled into gelatin capsule according to a conventional method or other methods, thereby preparing a capsule formulation.

4. Preparation of Pills

| | |
|---|---|
| The compound of chemical formula 1 | 1 g |
| Lactose | 1.5 g |
| Glycerin | 1 g |
| Xylitol | 0.5 g |

The above mentioned components were mixed and formed into pills with weight of 4 g according to a conventional method or other methods, thereby preparing a pill formulation.

5. Preparation of Granules

| | |
|---|---|
| The compound of chemical formula 1 | 150 mg |
| Extract of soybean | 50 mg |
| Glucose | 200 mg |
| Starch | 600 mg |

The above mentioned components were mixed and added with 100 mg of 30% ethanol. The mixture were dried at 60° C. and remained to form granules. The granules were filled into pouch, thereby preparing a granule formulation.

Accordingly, the composition of an exemplary embodiment has an excellent action of inhibiting the expression of AIMP2-DX2 and has an excellent effect of suppressing the proliferation of cancer cells, and thus is effective in cancer prevention or treatment. Further, the composition of an exemplary embodiment exhibited no cytotoxicity and was selective only to cancer cells, and thus the safety thereof was verified. Therefore, the composition of an exemplary embodiment can be used for the purpose of preventing and treating cancer disease, and thus is highly industrially applicable.

Hereinafter, an exemplary embodiment of the present invention will be described in detail with reference to examples.

However, the following examples are merely for illustrating certain aspects of the present invention, and are not intended to limit the scope of the present invention.

As an assay result of a structural formula, the compound of an exemplary embodiment was verified to be 1,4,7-Trioxa-10-azacyclododecane, 10-[4-methyl-2-[[(4-methylphenyl)sulfonyl]amino]-1-oxopentyl], and called C11.

Example 1

Preparation of the compound 1,4,7-Trioxa-10-azacyclododecane, 10-[4-methyl-2-[[(4-methylphenyl)sulfonyl]amino]-1-oxopentyl]-(9CI)

The compound was synthesized by the following process.

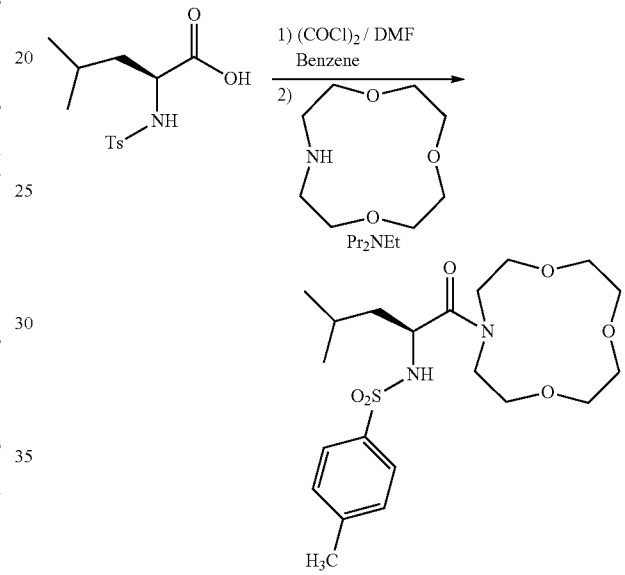

As an assay result of a structural formula, the compound was verified to be 1,4,7-Trioxa-10-azacyclododecane, 10-[4-methyl-2-[[(4-methylphenyl)sulfonyl]amino]-1-oxopentyl], and called C11.

Example 2

Investigation of Effect of the Compound on AIMP2-DX2 Activity

[Chemical formula 1]

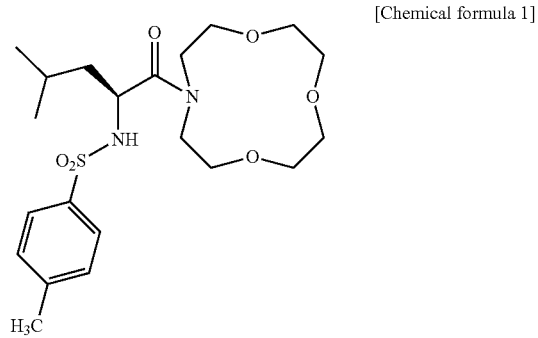 [SMILES: Cc1ccc(S(=O)(=O)N[C@@H](CC(C)C)C(=O)N2CCOCCOCCOCC2)cc1]

The present inventors conducted western blotting and RT-PCR using AIMP2 antibody and AIMP2-DX2 antibody (purchased from Neomics (Korea)) to verify the effect of the compound of chemical formula 1 on AIMP2-DX2 activity.

<2-1> Investigation of Effect on AIMP2-DX2 mRNA Level

H460 cells were treated with C11 with different concentrations, and then total-RNA was isolated according to the protocol of the manufacturer (Qiagen). The cells were collected, and mixed with 350 μl of a lysis buffer, which was then homogenized using a homogenizer or a syringe. After 350 μl of 70% ethanol was added, the lysate was shook above and below several times, and loaded on the column, followed by centrifuge at 13,000 RPM for 15 seconds. The column was washed twice with a washing buffer, and then RNA was eluted with 40 μl of RNase-free DW.

For reverse transcription, 1 μg of the isolated RNA was used as AIMP2-specific primers (SEQ ID NO: 2 and SEQ ID NO: 3) and DX2-specific primers (SEQ ID NO: 4 and SEQ ID NO: 5). After the reverse transcription, the product was diluted with 3-fold DW, and then 1 μl was used for 30 μl of PCR reaction including 0.5 μl dNTP (each 2.5 mM), 0.5 μl of the AIMP2 specific primer set (SEQ ID NO: 2 and SEQ ID NO: 3) and DX2 specific primers (SEQ ID NO: 4 and SEQ ID NO: 5) (each 10 pM), 1.5 μl of DMSO, and 0.1 μl of Taq polymerase (5 U/μl).

As shown in FIG. 1, the test results verified that the compound, C11, had no effect on the mRNA level of AIMP2-DX2.

<2-2> Investigation of Effect on AIMP2-DX2 Protein Level

A western blotting test was conducted to investigate the effect of C11 on the AIMP2-DX2 protein level.

H460 cells were treated with the compound, C11, for a predetermined period of time, and the protein was extracted from the cells using a RIPA buffer containing protease. The protein was isolated using 10 to 12% SDS-PAGE, and then immunoblotting was conducted using an ECL system as a specific antibody.

Figure 2:
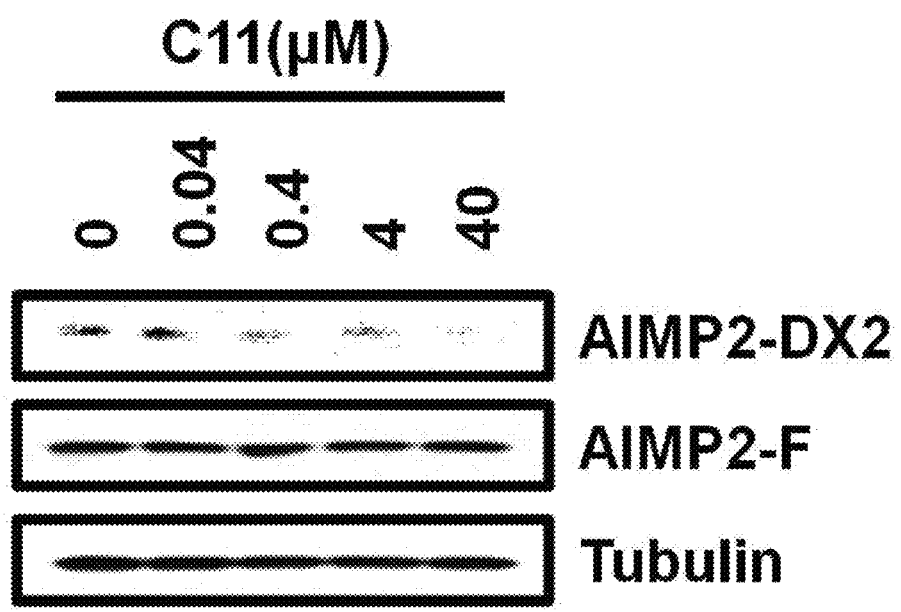
FIG. 2 shows Western blotting results verifying whether the compound of an exemplary embodiment of the present invention inhibits the protein level of AIMP2-DX2 in a concentration-dependent manner. Tubulin was used as a positive control (AIMP2-DX2: protein level of AIMP2++-DX2; AIMP2-F: protein level of full-length AIMP2 without exon deletion).

The results verified that the compound, C11, reduced the AIMP2-DX2 protein level in a concentration dependent manner, and had no effect on the AIMP2 protein expression (see FIG. 2).

The above results verified that the compound suppressed the expression of AIMP2-DX2, which is targeted by an anticancer drug, to inhibit AIMP2-DX2 activity.

Example 3

Evaluation of Cytotoxicity of C11 on Lung Cancer Cells (H460)

The present inventors conducted the following test to verify the lung cancer suppression effect of the compound, C11.

A lung cancer cell line NCI-H460 was cultured in an RPMI medium (HyQ RPMI-1640, Hyclone) containing 10% fetal bovine serum and 1% penicillin/streptomycin for 48 hours, and then transferred to a 96-well plate. After 12 hours, the medium was exchanged with the serum free RPMI medium, and then was treated with the compound of chemical formula 1 with 0.04 uM, 0.4 uM, 4 uM, and 40 uM. After 48 hours, MTT assay was conducted.

Figure 3:
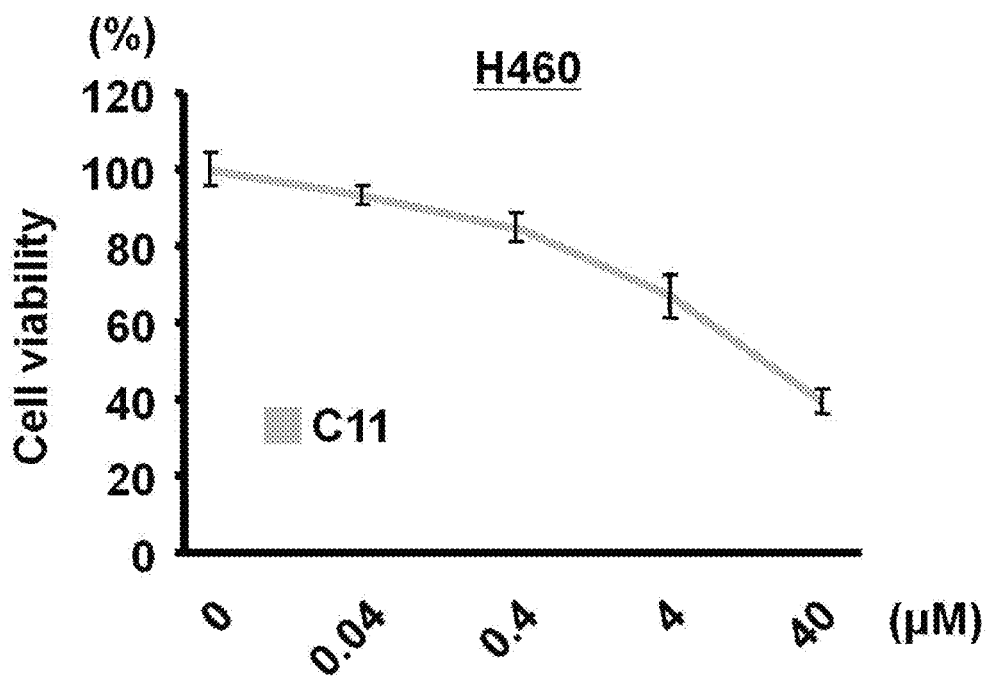
FIG. 3 is an MTT assay result graph verifying whether the compound of an exemplary embodiment of the present invention inhibits survival of a lung cancer cell line in a concentration dependent manner (Y axis: lung cancer cell line viability (%); X axis: concentration of the administered compound).

As shown in FIG. 3, the results verified that the lung cancer cells were killed by the compound, C11, in a concentration dependent manner.

Therefore, the compound, C11, can be used as a therapeutic agent for lung cancer by inhibiting the proliferation of lung cancer cells in a concentration dependent manner.

Example 4

Evaluation of Cytotoxicity of the Compound C11 on Normal Cell Line

In order to evaluate cytotoxicity of C11 on a normal cell line, WI-26, which is a human diploid fibroblast cell line from embryonic lung tissue, was treated with C11, and then cell viability was measured by MTT assay and compared with a control.

Figure 4:
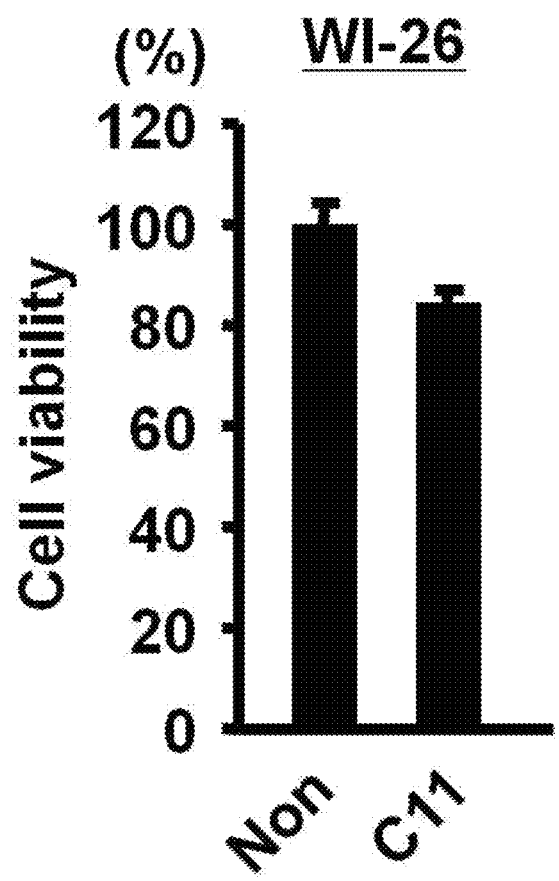
FIG. 4 is an MTT assay result graph verifying whether the compound of an exemplary embodiment of the present invention exhibits cytotoxicity on normal cells (WI-26) (Y axis: lung cancer cell line viability (%); C11: group administered with the compound; non: negative control).

As shown in FIG. 4, the results verified that when normal cells WI-26 were treated with the compound, C11, cytotoxicity was not observed.

Therefore, it was verified that the compound, C11, acts on only the lung cancer cell line without causing toxicity to normal cells, and thus can be safely used in lung cancer treatment.

What is claimed is:

1. A pharmaceutical composition, comprising a compound represented by Chemical Formula 1 or a pharmaceutically acceptable salt thereof as an active ingredient in an effective amount to treat a subject in need of lung cancer treatment, and
wherein Chemical Formula 1 is as follows:

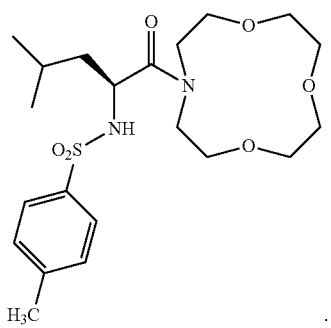

\<Chemical Formula 1\>

2. A method for treating lung cancer, the method comprising administrating an effective amount of a compound represented by Chemical Formula 1 or a pharmaceutically acceptable salt thereof to a subject in need of lung cancer treatment, wherein Chemical Formula 1 is as follows:

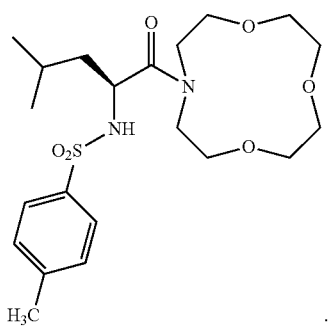

\<Chemical Formula 1\>

3. The pharmaceutical composition of claim 1, wherein the amount sufficient to treat the subject in need of lung cancer treatment is 0.1 to 1000 milligrams per day.

4. The pharmaceutical composition of claim 1, wherein the amount sufficient to treat the subject in need of lung cancer treatment is 1 to 500 milligrams per day.

5. The pharmaceutical composition of claim 1, wherein the subject in need is a mammal.

6. The pharmaceutical composition of claim 1, wherein the mammal is a human.

7. A pharmaceutical formulation, comprising:
a compound represented by Chemical Formula 1 or a pharmaceutically acceptable salt thereof as an active ingredient in an effective amount to treat a subject in need of lung cancer treatment, and
wherein Chemical Formula 1 is as follows:

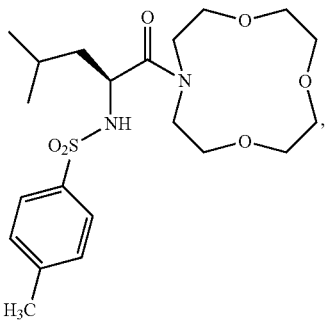

\<Chemical Formula 1\> wherein the pharmaceutical formulation is in the form of at least one of a liquid, a powder, a tablet, a capsule, a pill, or granules.

8. The pharmaceutical formulation of claim 7, further comprising lactose.

9. The pharmaceutical formulation of claim 8, wherein:
the pharmaceutical formulation is in the form of a powder,
the compound represented by Chemical Formula 1 is in an amount of 2 grams, and
the lactose is in an amount of 1 gram.

10. The pharmaceutical formulation of claim 8, further comprising cornstarch and magnesium stearate.

11. The pharmaceutical formulation of claim 10, wherein:
the compound represented by Chemical Formula 1 is in an amount of 100 milligrams,
the cornstarch is in an amount of 100 milligrams,
the lactose is in an amount of 100 milligrams, and
the magnesium stearate is in an amount of 2 milligrams.

12. The pharmaceutical formulation of claim 10, wherein the pharmaceutical formulation is in the form of a tablet or a capsule.

13. The pharmaceutical formulation of claim 8, further comprising glycerin and xylitol.

14. The pharmaceutical formulation of claim 13, wherein:
the pharmaceutical formulation is in the form of a pill,
the compound represented by Chemical Formula 1 is in an amount of 1 gram,
the lactose is in an amount of 1.5 grams,
the glycerin is in an amount of 1 gram, and
xylitol is in an amount of 0.5 grams.

15. The pharmaceutical formulation of claim 7, further comprising a soybean extract, glucose, and starch.

16. The pharmaceutical formulation of claim 15, wherein:
the pharmaceutical formulation is in the form of granules,
the compound represented by Chemical Formula 1 is in an amount of 150 milligrams,
the soybean extract is in an amount of 50 milligrams,
the glucose is in an amount of 200 milligrams, and
starch is in an amount of 600 milligrams.

* * * * *